United States Patent [19]

Myers, Jr. et al.

[11] 4,110,409

[45] Aug. 29, 1978

[54] PROCESS FOR MAKING CODIMERS OF NORBORNADIENE AND ALKYNES USING A COBALT CATALYST

[75] Inventors: Harry K. Myers, Jr., Aston; James E. Lyons, Wallingford; Abraham Schneider, Overbrook Hills, all of Pa.

[73] Assignee: Suntech, Inc., Wayne, Pa.

[21] Appl. No.: 842,812

[22] Filed: Oct. 17, 1977

[51] Int. Cl.² .................... C07C 13/28; C07C 15/12
[52] U.S. Cl. .................... 260/666 PY; 260/668 F; 149/109.4; 149/109.6
[58] Field of Search .................... 260/666 PY, 668 F; 149/109.4, 109.6

[56] References Cited

U.S. PATENT DOCUMENTS 3,978,147   8/1976   Wilke et al. .................... 260/666 PY

OTHER PUBLICATIONS

T. Mitsudo et al., J. Chem. Soc. Chem. Comm., pp. 722-723, 1976.
M. Hara et al., Tetrahedron, 1966.
A. Carbonaro et al., Tetrahedron Letters, 49, pp. 5129-5130, 1965.
T. Sasaki et al., J. Org. Chem. 37, No. 14, 1972.
Schrauzer et al., Chem. Ber. 97, pp. 2451-2462, 1964.

*Primary Examiner*—Veronica O'Keefe
*Attorney, Agent, or Firm*—J. Edward Hess; Donald R. Johnson; Anthony Potts, Jr.

[57] ABSTRACT

Norbornadiene and an alkyne are catalytically codimerized in the presence of a homogeneous catalytic system of cobaltic or cobaltous acetylacetonate, 1,2-bisdiphenylphosphino ethane and an alkyl aluminum chloride. Also, novel codimers of norbornadiene and an alkyne containing at least three carbons are disclosed. After hydrogenation, resulting codimers can be used as high energy fuels or diluents for such fuels.

11 Claims, No Drawings

PROCESS FOR MAKING CODIMERS OF NORBORNADIENE AND ALKYNES USING A COBALT CATALYST

BACKGROUND OF THE INVENTION

The invention herein described was made in the course of or under a contract with the United States Air Force Systems Command.

CROSS REFERENCE TO RELATED APPLICATION

This application is related to U.S. Application Ser. No. 842,813 filed at the same time by the above-identified inventors. Subject matter of related application is the reaction of norbornadiene and phenyl acetylenes.

The invention relates to the catalytic codimerization of norbornadiene and an alkyne. Particularly the invention relates to the preparation of an olefinic codimer of norbornadiene and an alkyne using a specified catalyst system. Hydrogenation of the resulting olefinic codimer yields a saturated codimer having utility as a high energy fuel or a diluent for such a fuel. The alkyne is referred to hereinafter as ALK.

High energy fuel, which is often referred to as a high density fuel, can be used in either jet or rocket propulsion. Jet propulsion includes a jet engine which can be used for a missile plane and others and includes the three basic types, i.e., ramjet, turbo-jet and pulse jet. The term rocket generally refers to a device containing its own oxygen or oxidizing agent.

Norbornadiene (I) is also known as bicyclo-(2.2.1) heptadiene-2,5. A method of preparation is disclosed in U.S. Pat. No. 2,875,256 issued Feb. 24, 1959. Hereinafter, norbornadiene is referred to as NBD. The latter can be represented by either one of the following structural formulas:

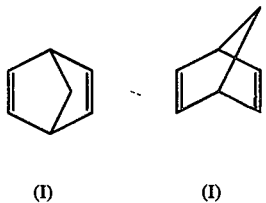

(I)    (I)

NBD can be easily dimerized to an hexacyclic dimer. Thus one problem in reacting NBD with another hydrocarbon reactant is to minimize the formation of the foregoing dimer while encouraging the formation of the desired codimer.

The reaction of norbornenes and acetylenes without using a catalyst has been referred to in J.C.S. Chem. Comm., 1976, pages 722–723, T. Mitsudo et al, in an article titled "Ruthenium-catalyzed [2 + 2] Cross addition of Norbornene Derivatives and Dimethyl Acetylene dicarboxylate". Such reactions are reported in Tetrahedron, 1966, M. Hara et al, "Photo-Addition-Reactions of Dimethyl Maleate and Dimethyl Acetylene Dicarboxylate with Norbornene". A. Carbonaro, et al in Tetrahedron Letters, 49, 1965, pages 5129–5130, "Oligomerization Catalysts-IV., Formation of Benzene Derivatives by Catalytic Reaction Between Norbornadiene and Acetylenic Hydrocarbons; A Core of Catalyzed Inverse DielsAlder Reaction", reports on the formation of aromatic compounds in the presence of iron catalysts. T. Sasaki et al in an article in the J. Org. Chem., Vol. 37, No. 14, 1972, titled "Studies on Reactions of Isoprenoids" reports on reactions of norbornadiene with unsymmetrically substituted acetylenic and heterodienophiles in the absence of a catalyst. Schrauzer et al, Chem.Ber., 97, 2451–2462, (1964), "Catalytic Addition of Olefins and Alkynes to Norbornadiene with $Ni^o$ Compounds and a new $Ni^{II}$ Complex as Catalysts", shows reaction of acetylene with norbornadiene. It should be noted that none of the aforementioned literature discloses the catalytic reaction herein disclosed.

SUMMARY OF THE INVENTION

NBD and ALK containing at least 3 carbon atoms are codimerized to a novel codimer II having the following structure:

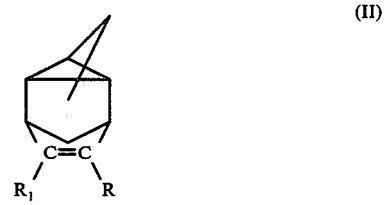

wherein $R_1$ is a $C_1$–$C_{10}$ paraffinic or iso alkyl and R is a hydrogen or a $C_1$–$C_{10}$ paraffinic or iso alkyl and wherein R and $R_1$ are interchangeable as to their location on the structure.

A codimer, including deltacyclene, is prepared by contacting NBD and ALK containing no more than 12 carbon atoms in the presence of a catalytic amount of homogeneous catalytic system of cobaltic or cobaltous acetylacetonate, 1,2-bisdiphenylphosphino ethane and one of three alkyl aluminum chlorides. The resulting codimer upon hydrogenation has utility as high density fuels or as a diluent for such a fuel.

DESCRIPTION

Cobaltic acetylacetonate ($Co(C_5H_7O_2)_3$) is referred to hereinafter as $CoA_3$ whereas the cobaltous form ($Co(C_5H_7O_2)_2$) is referred to as $CoA_2$. Collectively the two are referred to as CoA. The 1,2-bisdiphenylphosphino ethane is referred to as DIPHOS while the alkyl aluminum chloride is referred to as AAC.

The catalytic codimerization of NBD and ALK via present invention can be represented by the following formula reaction:

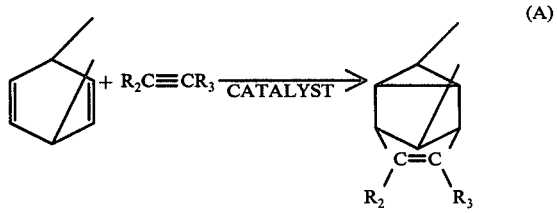

wherein both $R_2$ and $R_3$ are a $C_1$–$C_{10}$ paraffinic or iso alkyl or a hydrogen and wherein $R_2$ and $R_3$ are interchangeable. As shown NBD and ALK are contacted in the presence of a catalytic amount of the catalyst system defined herein. Examples of $R_2C{\equiv}CR_3$ include acetylene, propyne, butyne, pentyne-1, heptyne, octyne, decyne, pentyne-2, 3-methylbutyne-1, hexyne-2, and hexyne-3.

Wherein reaction A, one of the R's, for example R, is a hydrogen or a $C_1$-$C_{10}$ paraffinic or iso alkyl and the other R, for example $R_1$, is a $C_1$-$C_{10}$ paraffinic or iso alkyl, a novel codimer results. The resulting novel codimer has the following structural formula:

(II)

In structure II $R_1$ and R are interchangeable. Examples of $R_1C{\equiv}CR$ include propyne, butyne, pentyne-1, heptyne, octyne, decyne, pentyne-2, 3 methylbutyne-1, hexyne-2 and hexyne-3.

Hydrogenation of the codimer of NBD and ALK can be represented by the following formula reaction:

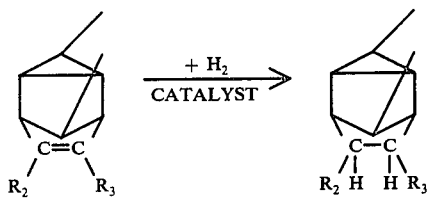

(B)

wherein each $R_2$ and $R_3$ are a $C_1$-$C_{10}$ paraffinic or iso alkyl or hydrogen. As an example the hydrogenation of the codimer deltacyclene (III) yields deltacyclane (IV). The latter two codimers have the following structure:

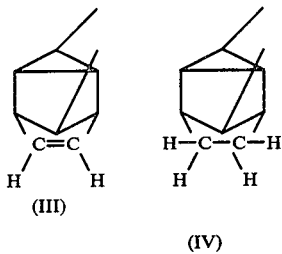

(III)     (IV)

The NBD used can contain a nominal amount of similar hydrocarbons, however, which if present should not be of a type which could adversely effect the reaction. If the NBD used contains undesirable hydrocarbons, they can be removed by known means. The foregoing also applies to the ALK used. In particular the ALK must be acetone-free because the latter deactivates the catalyst. For example, commercially available acetylene often contain traces of acetone because of the shipping methods used. Thus the hydrocarbons used in the invention can consist essentially of NBD and the ALK.

In the codimerization of NBD and ALK one mole of each reacts with the other to form one mole of the NBD-ALK codimer II. However, if the NBD to ALK mole ratio is too large homodimerization can occur with an adverse effect on codimer yields. On the other hand, if the NBD to ALK mole ratio is too low then the yield per pass can be too low and hence uneconomical. Within the aforementioned range a preferred NBD to AK mole ratio is in the range between from about 0.1 to about 500 with about 0.5 to about 50 more preferred.

The catalytic system favoring the aforementioned codimerization reaction A contains components which are commercially available and methods for their preparation are reported in the literature. The three are $CoA_3$ or $CoA_2$, DIPHOS and AAC. The AAC can be selected from the group consisting of diethylaluminum chloride, ethyl aluminum dichloride and ethyl aluminum sesquichloride. The latter three are referred to as DEAC, EADC and EASC, respectively. The amount of any component present is a catalytic amount so that a suitable conversion to codimer II occurs and the selectivity as to it is sufficient. Material, which during the codimerization reaction could adversely affect the catalyst system, should not be present. For example, the presence of hydroxylic compounds such as water, alcohol or oxygen from air could deactivate the catalyst system. Thus the catalytic system can consist of the aforementioned three components.

The amount of the CoA present should be catalytically sufficient to obtain the desired product. Generally the NBD to CoA mole ratio can range between from about 10 to about 2000 with a preferred range between from about 20 to about 1000.

Another component of the catalyst system is DIPHOS which has the following formula: $[(C_6H_5)_2PCH_2]_2$ The amount of this component of the catalyst system should be catalytically sufficient to obtain the desired product. Generally the DIPHOS to CoA mole ratio can range between from about 0.1 to about 5 with a preferred range between from about 1 to about 4.

DEAC, EADC or EASC is another component of the catalyst system with DEAC preferred. The amount of this component can vary substantially but generally it relates to the amount of CoA used. An effective DEAC, EADC or EASC to CoA mole ratio can be between from about 0.5 to about 100 with from about 1 to about 50 preferred and from about 3 to about 20 more preferred. Generally, when DEAC, EADC or EASC is used it is advantageous to conduct the reaction under substantially anhydrous conditions and under an inert gas blanket. Excess DEAC, EADC or EASC also serves as a scavenger.

Selectivity refers to the amount, mole or weight, of a particular compound formed divided by the amount of all compounds formed. From a commercial standpoint the economics of an overall process determines the optimal levels for both the selectivity and yield.

The reaction time required for an economically satisfactory selectivity and/or yield depends on a number of factors, such as catalyst to feed ratio, as well as operating conditions. Also the economics depend on capital investment versus conversion per pass and the like. The catalyst to feed ratios are discussed herein while typical conditions are provided by the Example.

A solvent can be used in the codimerization reaction. The solvent can be inert or it can be the NBD itself. Since the reaction is mildly exothermic the solvent can serve as a heat sink. It can also assist in solubilizing the reaction components, that is the feed and the components of the catalyst, and thereby provide for a homogeneous reaction medium. Some solvent can be added to the system as a carrier for one or more of the catalyst components. For example, DEAC is often maintained in an inert solvent such as toluene rather than NBD itself. Furthermore, the solvent should not adversely react with the feed, products or catalyst, therefore, if it is not NBD, it should be "inert". Also, presence of a solvent can facilitate the handling of the reaction mixture. Classes of suitable inert solvents include aromatic hydrocarbons, cycloparaffins, ethers, halogenated aromatics, halogenated paraffins and halogenated cycloparaffins. Specific examples include benzene, toluene, xylenes, cyclohexane, cyclopentane, diethylether, chlorobenzene, bromobenzene, chlorinated cyclohexane and the like. As to the amount of solvent used, excessive amounts decrease the reaction rate, and thus adversely affect the economics for a commercial operation.

The codimerization of NBD and ALK with the catalyst system can occur at ambient temperature. Thus the temperature of the homogeneous feed catalyst system mixture need not be raised to initiate reaction A. However, if the mixture is at an extremely low temperature, then heating of the cooled mixture could be necessary. Furthermore, once reaction A is underway, some heat is generated and the temperature of the mixture increases. If the temperature increases too much then some cooling would be required. Generally, however, the codimerization of NBD and ALK with a reasonable amount of the catalyst system is not characterized by an extremely rapid exotherm.

Selective codimerization of the NBD and ALK most efficiently occurs in a liquid phase and therefore it is not desirable to have the reaction temperature largely exceed the boiling points of the NBD and/or any solvent. Conversely, if the temperature is too low the reaction rate can be too low to be economically feasible. An operable temperature range is between from about $-20°$ C to about 100° C with about 25° C to about 85° C a preferred range. The operating pressure can vary substantially, however, it can generally range from about atmospheric up to about 2000 psi with about 1000 psi a preferred upper value. Furthermore, the upper limit depends in part on the particular ALK used, thus for example, the upper limit for acetylene would be about 250 psig. Also, safety consideration could require a lower upper limit. Process economics favor lower operating pressure, however, a moderately elevated reaction pressure may be desirable to keep the ALK in solution.

To further illustrate the invention, the following examples are provided.

EXAMPLES

The reaction of NBD and acetylene was carried out in the following manner. In a glass pressure vessel at 24° C, were mixed 0.02 millimoles of $CoA_3$ and 0.03 millimoles of DIPHOS each in 0.5 milliliter of benzene. The resulting green solution was deaerated with argon. Then 9.8 millimoles of deaerated NBD were added to the vessel. Following the latter addition, acetone-free acetylene gas was then passed through the green solution at a rate of approximately 20cc/minute. Then 0.4 millimoles of DEAC in solution (1.85 molar) in toluene were added to the pressure vessel and the vessel then immersed in a 35° C oil bath. A slight exotherm followed and the reaction liquid temperature rose to 42° C. Samples of the reaction mixture were taken at 30 minutes and 96 minutes. The samples were deactivated using 2-propanol, and then analyzed by vapor phase chromatography. The results are as follows:

| Time | % NBD as Codimer | % NBD as Binor-S | Other |
| --- | --- | --- | --- |
| 30 minutes | 17.0 | 2.6 | Trace |
| 96 minutes | 38.9 | 3.9 | Trace |

The resulting codimer was deltacyclene III. Similar results will be obtained if $CoA_2$ replaces $CoA_3$ in reaction A and/or the DEAC is replaced by EADC or EASC. Deltacyclene III is a colorless liquid boiling at 44° C at 0.19mm of Hg. It has a strained tetracyclic structure. Its density is about 1.007 grams/milliliter at 20/4° C. Its melting point is about $-35°$ C.

Deltacyclene III was hydrogenated at ambient temperature to deltacyclane IV using hydrogen and $PtO_2$ as the catalyst. The resulting deltacyclane had the following properties: boiling point of about 152°–153° C; density at 20/4° C of 0.96g/cc; and a refractive index (D20/4) of 1.4928. It was a liquid at room temperature and a solid below about $-30°$ C. Other useful hydrogenation catalysts are exemplified by platinum on carbon and nickel on kieselguhr.

Reactions of NBD and other ALK's i.e., propyne, butyne-1, hexyne-1, and hexyne-3 were carried out in an analogous manner. In all examples resulting structures were confirmed by infrared spectroscopy, nuclear magnetic resonance spectrometry and mass spectral analysis. The resulting codimers also may be hydrogenated using $PtO_2$ at ambient temperature.

Use of other ALK's such as pentyne-1, pentyne-2, 3-methylbutyne-1, and hexyne-2, in place of the aforementioned ALK will yield analogous results.

The invention claimed is:

1. Process for the catalytic codimerization of norbornadiene with an alkyne comprising:
    (a) contacting norbornadiene and an acetone free alkyne containing no more than 12 carbons in the presence of a catalytic amount of a homogeneous catalytic system of cobaltic or cobaltous acetylacetonate, 1,2-bisdiphenylphosphino ethane and one of the following alkyl aluminum chlorides: diethylaluminum chloride, ethyl aluminum dichloride and ethyl aluminum sesquichloride;
    (b) having the contacting occurring at a temperature within the range from between about $-20°$ C to about 100° C; and
    (c) continuing the contacting until the codimer of norbornadiene and the alkyne is prepared.

2. Process according to claim 1 wherein the bisdiphenylphosphino ethane to the acetylacetonate mole ratio is in the range between from about 0.1 to about 5.

3. Process according to claim 1 wherein the norbornadiene to the alkyne mole ratio is in the range between from about 0.1 to about 500.

4. Process according to claim 1 wherein the alkyl aluminum chloride to the acetylacetonate mole ratio is in the range between from about 0.5 to about 100.

5. Process according to claim 1 wherein the norbornadiene to the acetylacetonate mole ratio is in the range between from about 10 to about 2000.

6. Process according to claim 5 wherein an inert solvent is present.

7. Process according to claim 6 wherein the inert solvent is selected from the group consisting of aromatic hydrocarbons, cycloparaffin, ether, halogenated aromatic hydrocarbon, halogenated paraffin and halogenated cycloparaffin.

8. Process according to claim 7 wherein the bisdiphenylphosphino ethane to the acetylacetonate mole ratio is in the range between from about 0.1 to about 5.

9. Process according to claim 8 wherein the norbornadiene to the alkyne mole ratio is in the range between from about 0.1 to about 500.

10. Process according to claim 9 wherein the alkyl aluminum chloride to the acetylacetonate mole ratio is in the range between from about 0.5 to about 100.

11. Process according to claim 10 wherein the norbornadiene to the acetylacetonate mole ratio is in the range between from about 10 to about 2000.

* * * * *